United States Patent
Bombardelli et al.

(10) Patent No.: US 9,283,259 B2
(45) Date of Patent: Mar. 15, 2016

(54) **FORMULATIONS CONTAINING EXTRACTS OF *ECHINACEA ANGUSTIFOLIA* AND *ZINGIBER OFFICINALE* WHICH ARE USEFUL IN REDUCING INFLAMMATION AND PERIPHERAL PAIN**

(75) Inventors: Ezio Bombardelli, Gropello Cairoli (IT); Paolo Morazzoni, Milan (IT)

(73) Assignee: INDENA S.P.A., Milan (IT)

( * ) Notice: Subject to any disclaimer, the term of this patent is extended or adjusted under 35 U.S.C. 154(b) by 93 days.

(21) Appl. No.: 13/811,503

(22) PCT Filed: Jul. 20, 2011

(86) PCT No.: PCT/EP2011/062421
§ 371 (c)(1),
(2), (4) Date: Mar. 11, 2013

(87) PCT Pub. No.: WO2012/013551
PCT Pub. Date: Feb. 2, 2012

(65) Prior Publication Data
US 2013/0266672 A1    Oct. 10, 2013

(30) Foreign Application Priority Data

Jul. 26, 2010 (IT) .................................. MI10A1373

(51) Int. Cl.
| | | |
|---|---|---|
| *A61K 36/28* | (2006.01) | |
| *A61K 36/9066* | (2006.01) | |
| *A61K 36/185* | (2006.01) | |
| *A61K 36/9068* | (2006.01) | |
| *A61K 9/00* | (2006.01) | |
| *A61K 9/06* | (2006.01) | |
| *A61K 9/107* | (2006.01) | |
| *A61K 9/48* | (2006.01) | |
| *A61K 47/46* | (2006.01) | |

(52) U.S. Cl.
CPC ........... *A61K 36/9068* (2013.01); *A61K 9/0014* (2013.01); *A61K 9/06* (2013.01); *A61K 9/107* (2013.01); *A61K 9/4858* (2013.01); *A61K 36/28* (2013.01); *A61K 47/46* (2013.01)

(58) Field of Classification Search
CPC ...................... A61K 2300/00; A61K 36/9068
USPC .......................................... 424/756, 725, 773
See application file for complete search history.

(56) References Cited

U.S. PATENT DOCUMENTS

| | | | |
|---|---|---|---|
| 6,274,177 B1 * | 8/2001 | Wu et al. ........................ | 424/756 |
| 2001/0046523 A1 | 11/2001 | Newmark et al. | |
| 2010/0317565 A1 * | 12/2010 | Geiger et al. .................. | 514/1.5 |

FOREIGN PATENT DOCUMENTS

| | | |
|---|---|---|
| WO | 99/21007 A1 | 4/1999 |
| WO | 2005/053720 A1 | 6/2005 |
| WO | 2008/070783 A2 | 6/2008 |
| WO | 2010/083967 A1 | 7/2010 |

OTHER PUBLICATIONS

Tragni et al. (Evidence From Two Classic Irritation Tests For An Anti-Inflammatory Action Of A Natural Extract, Echinacina B, Fd. Chem Toxic. vol. 23, No. 2, pp. 317-319, 1985).*
International Search Report issued in counterpart International PCT Application No. PCT/EP2011/062421.
Vangasena, Vangasena, Page(s) being submitted—5 (pp. 4-8) (Ref.p. No. of publication:1024 ), Edn. 1996, Khemraj Shrikrishna Das Prakashan, Bombay. India.
Madanapala, Madanapalanighantauh, Page(s) being submitted—5 (pp. 9-13) ( Ref.p. No. of publication:65 ), Edn. 1998, Khemraj Shrikrishna Das Prakashan, Bombay, India.
Bharata Bhaishajya Ratnakara, Page(s) being submitted—5, (pp. 14-18) ( Ref.p. No. of publication:81 ), Edn. 2nd. Reprint, Aug. 1999, B. Jain Publishers, New Delhi, India.

* cited by examiner

*Primary Examiner* — Chris R Tate
*Assistant Examiner* — Randall Winston
(74) *Attorney, Agent, or Firm* — Silvia Salvadori, P.C.; Silvia Salvadori

(57) ABSTRACT

Disclosed is a combination of lipophilic extracts of *Zingiber officinale* and *Echinacea angustifolia* for the treatment of itching, peripheral pain, superficial and deep inflammatory and painful states, pain associated with muscle spasms, herpes pain, and radiodermatitis caused by oncological radiotherapy, with or without fungal or bacterial infections.

8 Claims, No Drawings

FORMULATIONS CONTAINING EXTRACTS OF *ECHINACEA ANGUSTIFOLIA* AND *ZINGIBER OFFICINALE* WHICH ARE USEFUL IN REDUCING INFLAMMATION AND PERIPHERAL PAIN

This application is a U.S. national stage of PCT/EP2011/062421 filed on Jul. 20, 2011, which claims priority to and the benefit of Italian Application No. MI2010A 001373, filed on Jul. 26, 2010, the contents of which are incorporated herein by reference.

SUMMARY OF THE INVENTION

The present invention relates to compositions containing lipophilic extracts of *Echinacea* spp. and *Zingiber officinale* which are useful in the topical treatment of itching, peripheral pain, superficial and deep inflammatory and painful states, and pain associated with muscle spasms. The formulations according to the invention are also particularly useful in the treatment of herpes pain and radiodermatitis caused by oncological radiotherapy, with or without fungal or bacterial infections.

The formulations can also be used in the cosmetic field to reduce oedema and irritative states of all kinds.

State of the Art

Lipophilic extracts of *Echinacea* spp., preferably those of *Echinacea angustifolia* described in EP 0464298, possess anti-inflammatory activity when administered either topically or systemically. It has been demonstrated that their pharmacological activity is attributable to isobutylamides, ligands of the CB1 and CB2 cannabinoid receptors.

Isobutylamides possess immunostimulating activity which characterises the traditional and pharmaceutical use of *Echinacea* extracts.

The roots and rhizomes of *Zingiber officinale*, variously treated, are used as spices in India and China. The uses described in traditional medicine include the treatment of indigestion, flatulence, diarrhoea, coughing, and other correlated disorders. The extracts of this plant were particularly considered for their antinausea effect. However, the data reported in controlled clinical trials are contradictory, and the US Pharmacopoeia recommends a complete review of the properties attributed to the plant due to the lack of convincing documentation. Some of the conflicting data are partly due to the instability of the active ingredients in the extracts normally used.

The extract used in the present invention is a lipophilic extract, stabilised and prepared with carbon dioxide under well-defined supercritical conditions.

DESCRIPTION OF THE INVENTION

It has now surprisingly been discovered that the combination of lipophilic or partly hydrophilic extracts of *Echinacea* spp roots and rhizomes with lipophilic extracts of *Zingiber officinale* produces a potent analgesic and anti-inflammatory activity, greater than can be obtained with uncombined extracts of *Echinacea* and *Zingiber officinale*.

The combination according to the invention can be used in the treatment of peripheral pain of all kinds, ranging from diabetic neuropathy to radiodermatitis, joint and muscle pain of different origins and herpes pain, even in the absence of specific antiviral treatment.

Lipophilic extracts of *Echinacea* spp can be obtained by extraction from the roots or rhizomes with alcohols, ketones or aliphatic ethers, or preferably with carbon dioxide under supercritical conditions.

Extracts of *Zingiber officinale* roots and rhizomes can also be obtained by extraction with carbon dioxide under supercritical conditions.

For the preparation of the extracts contained in the compositions according to the invention, simultaneous extraction of the finely ground roots and rhizomes of *Echinacea* spp. and *Zingiber officinale* with carbon dioxide under supercritical conditions is preferred, in varying ratios which are regulated according to the titre of the biomasses of the active ingredients, in particular according to the isobutylamide content for *Echinacea* (expressed as pellitorine or other specific isobutylamides) and the gingerol content for *Zingiber officinale*. The ratio of the two biomasses can range between 1:1 and 1:0.1, preferably 1:0.5. The extraction process with supercritical carbon dioxide guarantees the stability of the active components, preventing the formation of compounds such as shogaol and other inactive products of oxidation.

The finely ground biomasses are extracted for 1-10 hours, preferably 7 hours, at a temperature of between 40 and 60° C., preferably 50° C., and a pressure of between 200 and 260 bars, preferably 235 bars. The extract is collected in the condenser, and after elimination of water by solubilisation of the oily residue in ethyl acetate containing ascorbyl palmitate and dehydration on anhydrous sodium sulphate, it is concentrated until dry under vacuum at a temperature not exceeding 40° centigrade. The extract thus obtained can be directly diluted in oils in the presence of surfactants or phospholipids, or formulated with excipients suitable for administration to animals or humans.

In another embodiment, the invention provides a composition containing the combination of lipophilic or partly hydrophilic extracts of *Echinacea* spp roots and rhizomes with lipophilic extracts of *Zingiber officinale* as above described, together with physiologically compatible vehicles and excipients. In a preferred embodiment, the composition is in a form suitable for topical administration.

The composition according to the invention can be made by mixing the extracts obtained separately, so that the ratio between the isobutylamides obtained from *Echinacea* spp and gingerol from *Zingiber officinale* is between 1:1 and 1:0.1. For this purpose, an *Echinacea angustifolia* extract described in EP 0464298 can be used, and a lipophilic extract of *Zingiber officinale* prepared by extraction from the roots and rhizomes of the plant with carbon dioxide under supercritical conditions similar to those just described, extracting the powder from the roots and rhizomes at pressures of between 230 and 260 bars, preferably 235 bars, and a temperature of between 40 and 60° C., preferably 50° C., for a time ranging between 1 and 10 hours, preferably seven hours; the extract is collected in the condenser and dehydrated in inert gas dissolved in n-hexane or heptane containing a lipophilic antioxidant, preferably ascorbyl palmitate or tocopherol, and concentrated under vacuum at a temperature not exceeding 40° C.

The *Echinacea angustifolia* root extract typically contains 15 to 45% of isobutylamides, while the *Zingiber officinale* rhizome extract contains 15 to 30% gingerol together with other terpenes.

The topical compositions according to the invention typically contain 0.1 to 1% by weight of extracts of the two plant species, in particular 0.2 to 0.8% of the compound extract of the two species or 0.1 to 0.3% of *Zingiber officinale* extract and 0.2 to 0.5% of *Echinacea* extract.

The composition has proved particularly useful in the topical treatment of itching, peripheral pain, superficial and deep inflammatory and pain states and pain associated with muscle spasms. The formulations are also particularly useful in the treatment of herpes pain and radiodermatitis caused by oncological radiotherapy, with or without fungal or bacterial infections.

The compositions according to the invention can also be used in the cosmetic field to reduce oedema and irritative states of all kinds, including those caused by excessive exposure to sunlight.

The composition can be applied directly to the skin in the oil in which it is solubilised, or incorporated in creams or ointments suitable for administration. The treatment can be performed one to three times a day, applying a dose of 0.5-5 g of the topical formulation to the part of the body affected by the painful disorder.

The pharmaceutical or cosmetic compositions according to the invention will be formulated according to conventional techniques, such as those described in "Remington's Pharmaceutical Handbook", Mack Publishing Co., N.Y., USA. The examples below further illustrate the invention.

EXAMPLE 1

Oil Containing Compound Extract of *Echinacea angustifolia* and *Zingiber officinale*

| | |
|---|---|
| Extract of *Echinacea angustifolia* and *Zingiber officinale* (isobutylamides 10 mg/gingerol 1.3 mg) | 0.3 g |
| Vitamin E | 1.0 g |
| Argan oil | q.s. for 100 ml |

EXAMPLE 2

Oil/Water Emulsion Containing Compound Extract of *Echinacea angustifolia* and *Zingiber officinale*

| | |
|---|---|
| Extract of *Echinacea angustifolia* and *Zingiber officinale* (isobutylamides 10 mg/gingerol 1.3 mg) | 0.5 g |
| Ascorbyl palmitate | 0.5 g |
| Evening primrose oil | 4.0 g |
| Polyethylene glycol-20-glyceryl stearate | 10.0 g |
| C10-C18 triglycerides | 10.0 g |
| Glycerin | 5.0 g |
| Hydroxylated lanolin | 0.5 g |
| Hydroxyethylcellulose | 0.5 g |
| Parabens | 0.2 g |
| Demineralised water | q.s. for 100.0 g |

EXAMPLE 3

Cream Containing Compound Extract of *Echinacea angustifolia* and *Zingiber officinale*

| | |
|---|---|
| Extract of *Echinacea angustifolia* and *Zingiber officinale* (isobutylamides 20 g/gingerol 2.6 g) | 0.6 g |
| Vitamin E | 1.0 g |
| Linseed oil | 4.0 g |
| Stearic acid | 12.0 g |
| Glycerin | 10.0 g |
| Cetostearyl alcohol | 2.0 g |
| Potassium hydroxide | 0.9 g |
| Parabens | 0.2 g |
| Demineralised water | q.s. for 100.0 g |

EXAMPLE 4

Oil Containing Extracts of *Echinacea angustifolia* and *Zingiber officinale*

| | |
|---|---|
| *Echinacea angustifolia* extract | 0.2 g |
| *Zingiber officinale* extract | 0.1 g |
| Ascorbyl palmitate | 1.0 g |
| Argan oil | q.s. for 100 ml |

EXAMPLE 5

Preparation of Compound Extract of *Echinacea angustifolia* and *Zingiber officinale*

10 Kg of a mixture of *Zingiber officinale* roots containing approx. 3% gingerol (1 part) and *Echinacea angustifolia* roots containing approx. 1% isobutylamides (3 parts) is finely ground and extracted with carbon dioxide under supercritical conditions at a temperature of 50° C. and a pressure of 235 bars for 7 hours. After extraction, the solvent is eliminated and the extracted material, consisting of an oily residue, is recovered in the condenser and taken up with 1.5 L of ethyl acetate containing 0.5 g of ascorbyl palmitate. The organic solution is dehydrated on $Na_2SO_4$ and concentrated under vacuum at a temperature not exceeding 30° C. 110 g of a thick, dark yellow oil with a 20% isobutylamide and 12% gingerol content is obtained. This extract can be used "as is" in pharmaceutical and cosmetic formulations.

EXAMPLE 6

Preparation of Lipophilic Extract of *Zingiber officinale*

10 Kg of *Zingiber officinale* roots containing approx. 1.2% gingerol is finely ground and extracted with carbon dioxide under supercritical conditions at a temperature of 50° C. and a pressure of 235 bars for 7 hours. After extraction, the solvent is eliminated and the extracted material, consisting of an oily residue, is recovered in the condenser and taken up with 1.5 L of hexane containing 0.5 g of ascorbyl palmitate. The organic solution is dehydrated on $Na_2SO_4$ and concentrated under vacuum at a temperature not exceeding 40° C. 400 g of a thick, dark yellow oil with a 20% gingerol content is obtained. This extract can be used "as is" in pharmaceutical and cosmetic formulations.

EXAMPLE 7

Evaluation of Analgesic Activity in the Rat

The analgesic activity of the composition according to the invention was evaluated with the tail-flick test in the rat. Before treatment, 3 basic measurements were conducted on the animals to ensure that they were suitable for the handling and apparatus involved. The parameters used were 15V of radiant heat and a 15-second cut-off (to prevent irreversible harm to the animals), with evaluation of the tail-flick. The animals were treated with 0.1 ml of oil according to the composition described in example 4, 5 cm from the start of the tail. The analgesic effect was measured 15 and 30 min. after administration. The two individual ingredients of the composition were evaluated with the same experimental model, in a formulation which contained the same amount of active ingredient as the composition described in example 4. The control animals were treated with 0.1 ml of the oil used to dissolve the two ingredients (carrier). The results are set out in Table 1 below.

TABLE 1

| | Latency time | | | |
|---|---|---|---|---|
| Treatment | after 15 min. | % increase | after 30 min. | % increase |
| Carrier | 4.5 ± 0.33 | — | 4.6 ± 0.45 | — |
| Composition described in example 4 | 12.6 ± 0.61 | 180 | 8.5 ± 0.43 | 84.8 |
| Echinacea angustifolia lipophilic extract | 6.1 ± 0.44 | 35.5 | 4.8 ± 0.63 | 4.4 |
| Zingiber officinale Lipophilic extract | 4.2 ± 0.63 | — | 4.6 ± 0.48 | — |

EXAMPLE 8

Evaluation of Analgesic Activity in Patients Suffering from Osteoarthritis of the Knee 40 patients suffering from osteopathy of the knee with constant pain were randomised and treated topically with the oil described in example 1, a placebo (consisting of the carrier alone), or the individual ingredients dissolved in the placebo at the same concentrations as in the oil described in example 1. Efficacy was evaluated on an international analog pain scale with scores from 0 to 10 points, 10 indicating maximum pain and 0 the disappearance of pain. The effect was evaluated 15 and 60 minutes after treatment.

The results are set out in Table 2 below.

TABLE 2

| | Pain (scores) at time | | |
|---|---|---|---|
| Treatment | 0 | 15 min. | 60 min. |
| Carrier | 8.3 ± 1.7 | 9.1 ± 2.2 | 8.2 ± 1.9 |
| Composition described in example 1 | 9.4 ± 2.6 | 4.3 ± 0.9 | 2.5 ± 1.4 |
| Echinacea angustifolia lipophilic extract | 8.7 ± 1.4 | 7.1 ± 1.4 | 7.8 ± 2.6 |
| Zingiber officinale Lipophilic extract | 8.2 ± 1.6 | 7.2 ± 0.6 | 8.6 ± 1.8 |

EXAMPLE 9

Effect on Radiation-Induced Itching 10 patients suffering from erythema caused by ultraviolet rays were treated with the quantity of a 0.1% solution in olive oil of the extract described in example 1 required to cover the irritated area. The irritation was significantly reduced only 15 minutes after application, while the itching disappeared immediately after application. The carrier proved to have no activity under the same conditions.

EXAMPLE 10

Soft Gelatine Capsules

Unit Composition:

| | |
|---|---|
| Lipophilic extract of Zingiber officinale | 12.5 mg |
| Lipophilic extract of Echinacea angustifolia | 5.0 mg |
| Soya lecithin | 10.0 mg |
| Flaxeed oil | 110.0 mg |

EXAMPLE 11

Evaluation of Analgesic Activity in Patients Suffering from Osteoarthritis of the Knee 60 patients suffering from osteopathy of the knee with constant pain were randomised and treated orally with the capsules described in example 10, a placebo (consisting of the carrier alone), or the individual ingredients dissolved in the placebo at the same amount as in the capsules described in example 10. Efficacy was evaluated on an international analog pain scale with scores from 0 to 10 points, 10 indicating maximum pain and 0 the disappearance of pain. The effect was evaluated 60 and 120 minutes after treatment.

The results are set out in Table 3 below.

TABLE 3

| | Pain (scores) at time | | |
|---|---|---|---|
| Treatment | 0 | 60 min. | 120 min. |
| Carrier | 7.6 ± 0.9 | 8.9 ± 1.2 | 7.4 ± 1.9 |
| Capsules of example 10 | 8.3 ± 1.6 | 3.5 ± 1.9 | 2.1 ± 0.6 |
| Echinacea angustifolia lipophilic extract | 8.1 ± 0.9 | 8.1 ± 1.6 | 7.9 ± 1.6 |
| Zingiber officinale Lipophilic extract | 7.9 ± 1.1 | 7.7 ± 0.9 | 7.6 ± 0.9 |

The invention claimed is:

1. A method of treating a condition selected from the group consisting of itching, peripheral pain, superficial or deep inflammatory and painful conditions, pain connected with muscular spasms, herpes pain, radiodermatitis induced by oncological radiotherapy, oedema and irritative skin conditions in a human in need thereof, said method comprising topically applying an effective amount of a combination of lipophilic extracts of Zingiber officinale and Echinacea angustifolia to the skin of said human.

2. The method of claim 1, wherein said effective amount comprises a dose of 0.5-5 g.

3. The method of claim 1, wherein said effective amount is applied one to three times a day.

4. The method of claim 1, wherein the extracts of both species are obtained by extraction from roots or rhizomes with supercritical carbon dioxide.

5. The method of claim 1, wherein the combination contains isobutylamides from Echinacea angustifolia and gingerol from Zingiber officinale in weight ratios ranging from 1:1 to 1:0:1.

6. The method of claim 1, wherein the combination contains isobutylamides from Echinacea angustifolia and gingerol from Zingiber officinale in weight ratios ranging of 1:0:5.

7. A method of treating a condition selected from the group consisting of itching, peripheral pain, superficial or deep inflammatory and painful conditions, pain connected with muscular spasms, herpes pain, radiodermatitis induced by oncological radiotherapy, oedema and irritative skin conditions in a human in need thereof, said method comprising topically applying an effective amount of a composition containing a combination of lipophilic extracts of *Zingiber officinale* and *Echinacea angustifolia* together with one or more physiologically-compatible vehicles and excipients to said human.

8. The method of claim 7, wherein the extracts are formulated in oils in the presence of surfactants or phospholipids.

\* \* \* \* \*